United States Patent
Zong et al.

(10) Patent No.: US 10,752,652 B2
(45) Date of Patent: Aug. 25, 2020

(54) METHOD FOR PREPARING A β-NUCLEOSIDE COMPOUND

(71) Applicant: JIANGSU AOSAIKANG PHARMACEUTICAL CO., LTD., Nanjing, Jiangsu (CN)

(72) Inventors: Zaiwei Zong, Nanjing (CN); Qian Zhao, Nanjing (CN); Ruifeng Yang, Nanjing (CN); Gan Li, Nanjing (CN); Chao Yi, Nanjing (CN); Haixi Zhu, Nanjing (CN)

(73) Assignee: JIANGSU AOSAIKANG PHARMACEUTICAL CO., LTD., Nanjing, Jiangsu (CN)

( * ) Notice: Subject to any disclaimer, the term of this patent is extended or adjusted under 35 U.S.C. 154(b) by 0 days.

(21) Appl. No.: 16/465,418

(22) PCT Filed: Dec. 21, 2017

(86) PCT No.: PCT/CN2017/117596
§ 371 (c)(1),
(2) Date: May 30, 2019

(87) PCT Pub. No.: WO2018/113710
PCT Pub. Date: Jun. 28, 2018

(65) Prior Publication Data
US 2019/0345189 A1 Nov. 14, 2019

(30) Foreign Application Priority Data
Dec. 23, 2016 (CN) .......................... 2016 1 1208029

(51) Int. Cl.
*C07H 19/12* (2006.01)
*C07H 1/06* (2006.01)

(52) U.S. Cl.
CPC .............. *C07H 19/12* (2013.01); *C07H 1/06* (2013.01)

(58) Field of Classification Search
CPC .. C07H 1/00; C07H 1/06; C07H 19/12; Y02P 20/55
See application file for complete search history.

(56) References Cited

U.S. PATENT DOCUMENTS

| 3,350,388 A | 10/1967 | Sorm et al. | |
| 3,817,980 A | 6/1974 | Vorbruggen et al. | |
| 4,082,911 A * | 4/1978 | Vorbruggen | C07H 19/04 536/27.11 |
| 8,212,021 B2 * | 7/2012 | Henschke | A61P 35/00 536/28.3 |

FOREIGN PATENT DOCUMENTS

| CN | 101307084 A | 11/2008 |
| CN | 101948493 A | 1/2011 |
| CN | 101987858 A | 3/2011 |
| CN | 102216315 A | 10/2011 |
| CN | 103524584 A | 1/2014 |
| CN | 108239128 A | 7/2018 |
| WO | 98/17281 A1 | 4/1998 |
| WO | 2010/017547 A1 | 2/2010 |

OTHER PUBLICATIONS

Mar. 23, 2018 International Search Report issued International Patent Application PCT/CN2017/117596.
A. Piskalaa et al.; "Direct synthesis of 5-azapyrimidine 2'-deoxribonucleosides. Hydrolysis of 5-aza-2'-deoxycytidine"; Nucleic Acids Research; Special Publication No. 4; Oct. 31, 1967; pp. s109-s114.

* cited by examiner

*Primary Examiner* — Lawrence E Crane
(74) *Attorney, Agent, or Firm* — Oliff PLC

(57) ABSTRACT

A method for preparing a β-nucleoside compound, including the following steps: 1) performing a silylation reaction of a nitrogenous base or an analogue thereof in the presence of TMSOTf to give the nitrogenous base or the analogue thereof being protected by trimethylsilyl; 2) performing a direct glycosylation reaction of the reaction liquid, without being isolated, and a five- or six-membered ring saccharide or a derivative thereof closed by a hydroxyl protecting group to give a closed β-nucleoside compound; and 3) performing a deprotection reaction to give the β-nucleoside compound. The method uses a one-pot process to prepare the key intermediates of the β-nucleoside compound, and the yield of materials in β-configuration increases significantly. The method has the benefits of simple operations, being energy conservation and environment protection, and being suitable for industrial applications.

19 Claims, No Drawings

METHOD FOR PREPARING A β-NUCLEOSIDE COMPOUND

CROSS-REFERENCE TO RELATED APPLICATIONS

Not applicable.

TECHNICAL FIELD

The present invention relates to the field of pharmaceutical chemistry, specifically relates to a method for preparing a β-nucleoside compound.

BACKGROUND

Nucleoside is a glucoside formed by the condensation of purine and pyrimidine bases with a cyclic ribose or deoxyribose. The saccharide is linked with bases through glucoside bonds, that is, the carbon atom at position 1 (C1) of the ribose or deoxyribose is linked with the nitrogen atom at position 1 (N1) of the pyrimidine base or the nitrogen atom at position 9 (N9) of the purine base. The saccharide has both α- and β-configurations, as C1 in the saccharide ring is an asymmetrical carbon atom.

Native nucleosides are all in β configuration, which are key ingredients constituting the life macromolecule RNA and DNA, are native metabolism activators, directly enter the cells to participate in the saccharide metabolism and promote the synthesis of proteins, promote the morbid cells and tissues to restore their normal physiological functions. Modified and engineered nucleoside compounds, the structures of which were very similar to that of native nucleoside, have currently been considered as the chemotherapeutic agents with the greatest potential, with good activities of anti-viral, anti-tumor, immunomodulation or anti-bacterial, etc. For example, the known nucleoside antitumor drugs include Decitabine, Gemcitabine, Azacitidine, Capecitabine, Fludarabine or the like. The known nucleoside anti-viral drugs include Lamivudine, Zidovudine, Telbivudine, Entecavir, Emtricitabine, Fomivirsen or the like.

In recent years, the development of nucleoside analogues with low toxicity, high anti-tumor and anti-viral activities has become the study focus, especially the single enantiomer in β-configuration has received widespread attention. As nucleoside analogues in β-configuration have better similarity with native nucleosides, it has been the technical difficulty that needs to be resolved and improved on how to synthesize nucleoside analogues in β-configuration stereoselectively with a more economical process.

Take decitabine for example, the drug is a 2'-deoxycytidine analogue developed by SuperGen Co., USA, marketed first in USA in 2006, useful for treating myelodysplastic syndrome in clinic. Currently, there are two main synthetic methods:

Method 1 (U.S. Pat. No. 3,350,388; *J. Org. Chem.*, 1974, 39, 3672-3674): Intermediate 2' was prepared with 3,5-di-O-p-toluene formyl-1,2-deoxy-β-D-arabinofuranosyl isocyanate and S-methyl isothiourea as the raw materials, which was then reacted with triorthoformate through a cyclization reaction to give 1-(3,5-di-O-p-toluene formyl-1,2-deoxy-β-D-arabinofuranosyl)-4-methyl-2-mercapto-2-oxo-1,2-dihydro-1,3,5-triazine (intermediate 3'), which was reacted with ammonia/methanol to give the intermediate 4', and finally deprotected by sodium methoxide/methanol to give Decitabine. Its synthesis route was as follows:

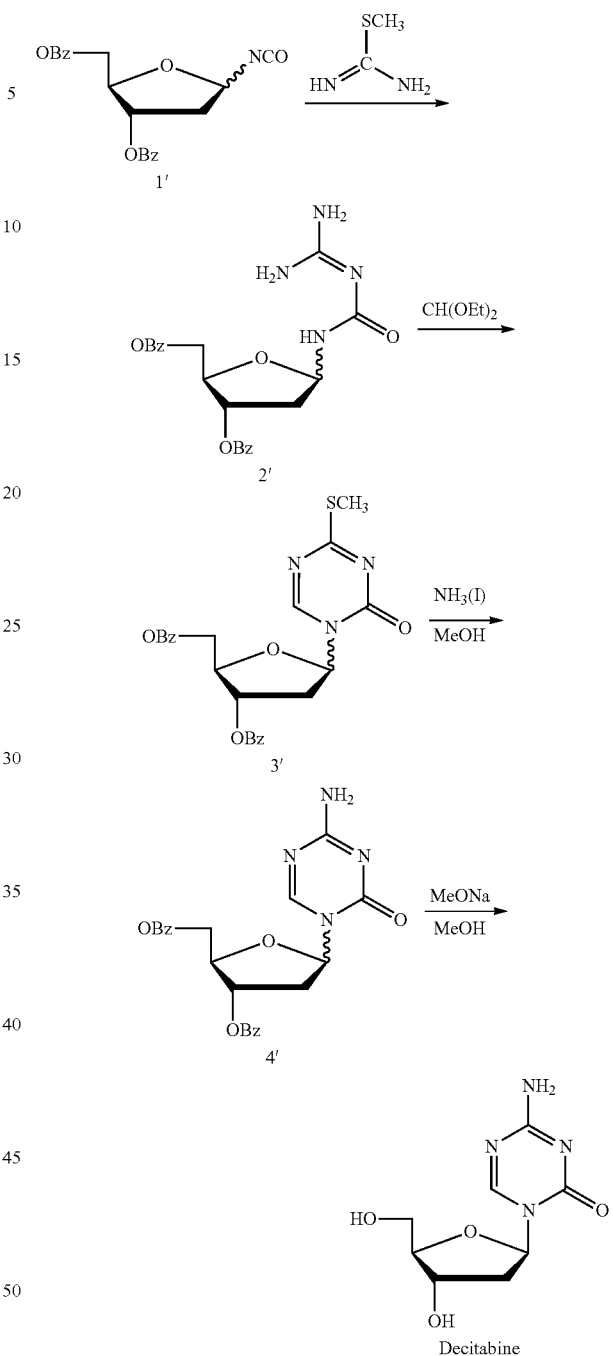

This route was complex in design, used many chemical reagents, and cumbersome in operation, not meeting the production requirement of low consumption and high efficiency.

Method 2 (*Nucl Acid Res*, 1978, s4, 109-113): Silyl ether B was prepared at reflux with 5-azacytosine A as the raw material and with hexamethyldisilazane (HMDS) as the silyl etherification reagent and the solvent, which was then condensed with chlorinated deoxyribose C under the catalysis of trimethylsilyl trifluoromethanesulfonate (TMSOTf) to give the intermediate D, which was then deprotected by sodium methoxide/methanol to give Decitabine. Its synthesis route was as follows:

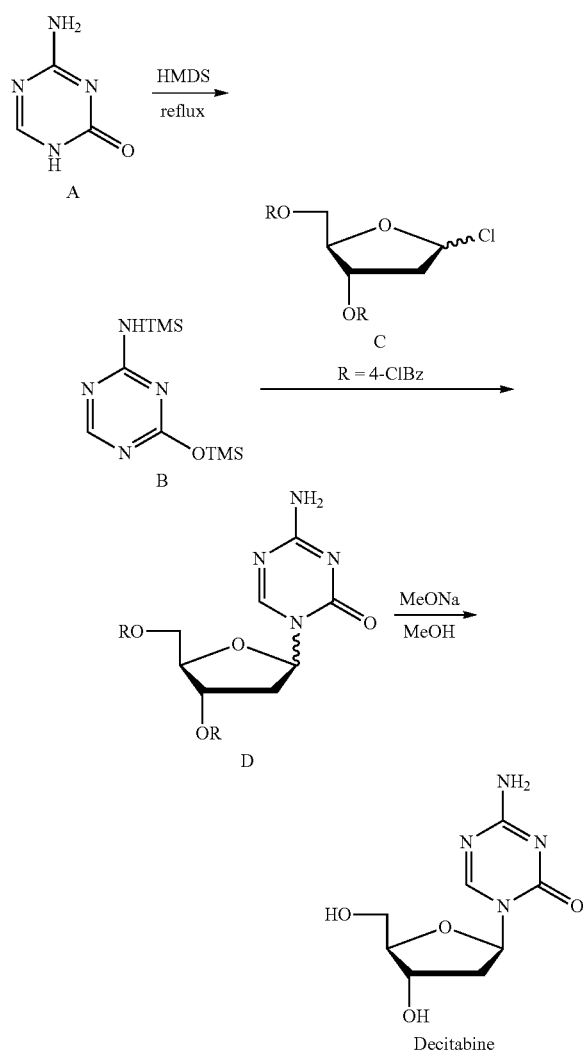

This route is the most common route in the industrial production of decitabine currently, in which the reaction steps are less than those in method 1, but there remains many problems: 1) HMDS was used heavily as the solvent, a large amount of ammonia was produced during the preparation of silyl ether 2, polluting the production environment seriously; 2) the excess amount of HMDS has to be removed from the reaction liquid through concentration, until a pasty mixture difficult to stir was obtained, the residue of which tend to cure during the concentration, easily causing the stirring system to be operated irregularly or be broken, not applicable for the production on the industrial level; 3) HMDS was difficult to be removed absolutely, which remains in silyl ether B and leads to the severe reduction of the β/α proportion of the intermediate D during the synthesis of the intermediate D, and very low yield of materials in β configuration.

Currently, the synthesis of other nucleoside drugs also generally use HMDS as the silylating agent to protect the active hydrogen on the base, the synthesis route or its path was substantially the same as the above route 2, and there remains the same technical problems.

Therefore, effective methods for producing β-nucleoside compounds remain to be insufficient in the prior art, it has become an urgent problem to be solved on the general stereoselective synthesis of the bioactive β-nucleoside compounds.

SUMMARY OF THE INVENTION

The present invention aims to provide a method for preparing a nucleoside compound, in which the two reactions of silylation and glycosylation could be carried out successively in a "one-pot" process, in which the reaction route was short, post-processing operations were simple, being environment-friendly, and the field of 3-isomers was enhanced significantly, suitable for the industrial production applications.

According to the above purposes, the present invention provides the following technical schemes:

A method for preparing a β-nucleoside compound, comprising the following steps:

1) performing a silylation reaction of a nitrogenous base or an analogue thereof in the presence of trimethylsilyl trifluoromethanesulfonate (TMSOTf) to give the nitrogenous base or the analogue thereof being protected by trimethylsilyl;

2) performing a direct glycosylation reaction of the reaction liquid of step 1, without being isolated, and a five- or six-membered ring saccharide or a derivative thereof closed by a removable protecting group to give a closed β-nucleoside compound;

3) performing a deprotection reaction of the closed β-nucleoside compound to give the β-nucleoside compound.

The nitrogenous bases of the present invention include purine and pyrimidine bases or derivatives thereof. The nitrogenous bases or the analogues thereof comprise groups that could react with TMSOTf in a silylation reaction, for example amino, hydroxy, carbonyl or the like.

In an exemplary embodiment, the nitrogenous base or the analogue thereof is selected from:

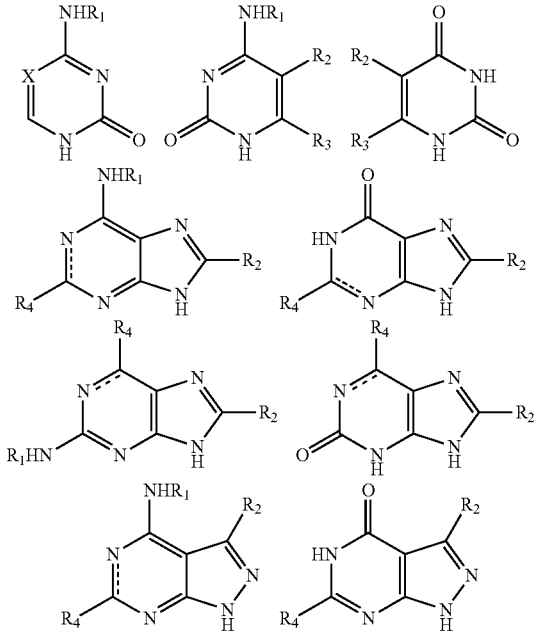

-continued

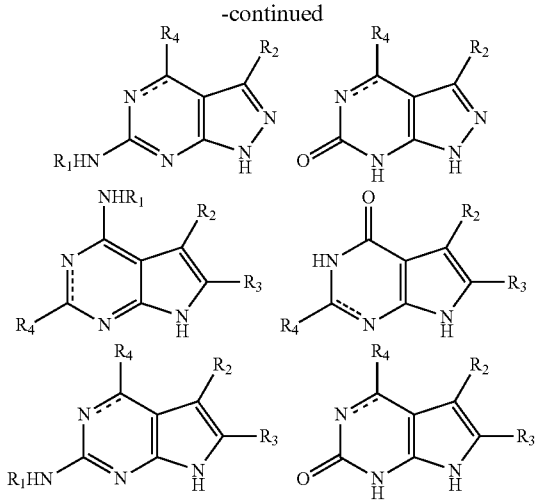

wherein: $R_1$ is selected from hydrogen, $C_{1-6}$ alkyl or a substituted alkyl, $C_{3-8}$ cycloalkyl or a substituted cycloalkyl; preferably, $R_1$ is selected from hydrogen, methyl, ethyl, propyl, cyclopropyl;

X is selected from nitrogen, CH, $CR_2$; preferably, X is selected from nitrogen, CH, $C(CH_3)$, $C(CH_2CH_3)$, $C(CH_2CH_2CH_3)$, $C(CH_2OH)$, $C(CF_3)$, $C(F)$, $C(Cl)$, $C(Br)$, $C(I)$;

$R_2$ and $R_3$ are independently selected from hydrogen, $C_{1-6}$ alkyl or a substituted alkyl, halogen; preferably, $R_2$ and $R_3$ are independently selected from hydrogen, methyl, ethyl, propyl, trifluoromethyl, hydroxymethyl, halogen;

$R_4$ is selected from hydrogen, $C_{1-6}$ alkyl or a substituted alkyl, halogen, amino, $NHR_1$, carbonyl; preferably, $R_4$ is selected from hydrogen, methyl, ethyl, propyl, hydroxymethyl, halogen, amino, carbonyl;

a dotted line bond indicates the presence or absence of a double bond.

More preferably, the nitrogenous base or the analogue thereof is selected from:

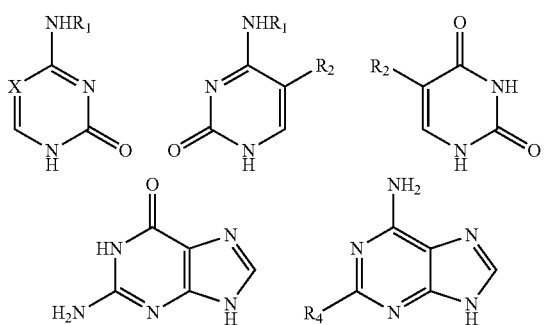

wherein: X, $R_1$, $R_2$, $R_4$ were defined as above.

Five- or six-membered ring saccharides of the present invention may be the saccharides known in the art. Five-membered ring saccharides are also known as furanose, six-membered ring saccharides are also known as pyranose.

In an exemplary embodiment, the five-membered ring saccharides or the derivatives thereof closed by a removable protecting group have the structures as shown in the following formula (I):

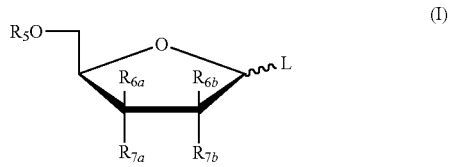

or, the six-membered ring saccharides or the derivatives thereof being protected by a removable protecting group have the structures as shown in the following formula (II):

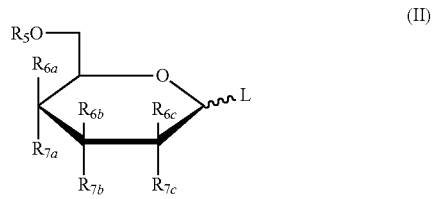

In formula (I) and formula (II): L is a leaving group; $R_5$ is a hydroxy protecting group; $R_{6a}$, $R_{6b}$, $R_{6c}$, $R_{7a}$, $R_{7b}$, $R_{7c}$ may independently be selected from hydrogen, halogen, $C_{1-6}$ alkyl or a substituted alkyl, $OR_5$, and $R_{6a}$ is $OR_5$ when different from $R_{7a}$, $R_{6b}$ is $OR_5$ when different from $R_{7b}$, $R_{6c}$ is $OR_5$ when different from $R_{7c}$.

More preferably, the five-membered ring saccharides or the derivatives thereof have the structures as shown in the following formula (I'):

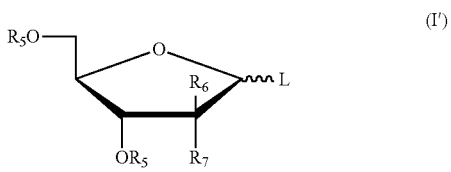

wherein: L is a leaving group; $R_5$ is a hydroxy protecting group; $R_6$ and $R_7$ may independently be selected from hydrogen, halogen, $C_{1-6}$ alkyl or a substituted alkyl, or one of which is $OR_5$.

More preferably, the six-membered rings or the derivatives thereof have the structures as shown in the following formula (II'):

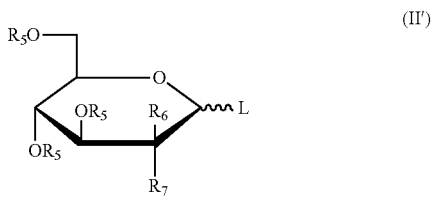

wherein: L, $R_5$, $R_6$, $R_7$ were defined as above.

According to the above methods of the present invention, which comprise: providing a method for preparing a closed β-nucleoside compound in a "one-pot" process, and a method of performing a deprotection reaction of a closed β-nucleoside compound to give a β-nucleoside compound.

In an exemplary embodiment, the present invention provides a method for preparing a closed β-nucleoside compound, the closed β-nucleoside compound has a structure as shown in formula (III) or formula (IV):

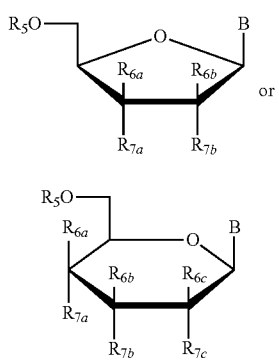

wherein, B indicates a nitrogenous base or an analogue thereof; $R_5$ is a hydroxy protecting group; $R_{6a}$, $R_{6b}$, $R_{6c}$, $R_{7a}$, $R_{7b}$, $R_{7c}$ may independently be selected from hydrogen, halogen, $C_{1-6}$ alkyl or a substituted alkyl, or one of $R_{6a}$ and $R_{7a}$ is $OR_5$, or one of $R_{6b}$ and $R_{7b}$ is $OR_5$, or one of $R_{6c}$ and $R_{7c}$ is $OR_5$;

The method includes the following steps:

1) performing a silylation reaction of a nitrogenous base or an analogue thereof in the presence of trimethylsilyl trifluoromethanesulfonate (TMSOTf) to give the nitrogenous base or the analogue thereof being protected by trimethylsilyl;

2) performing a direct glycosylation reaction of the reaction liquid of step 1), without being isolated, and a five- or six-membered ring saccharide or a derivative thereof closed by a removable protecting group to give a closed β-nucleoside compound as shown in formula (III) or formula (IV).

The nitrogenous base or the analogue thereof was defined as above.

The five- or six-membered ring saccharides or the derivatives thereof were defined as above.

Preferably, the nitrogenous base or the analogue thereof is selected from:

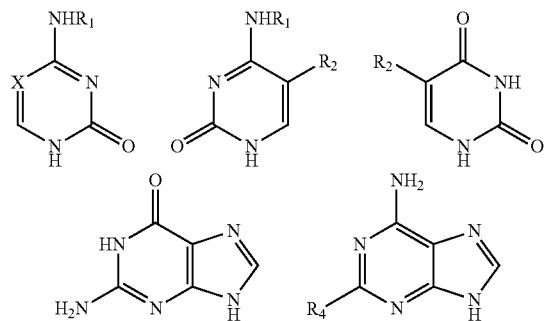

wherein: X, $R_1$, $R_2$, $R_4$ were defined as above.

Preferably, the five-membered ring saccharides or the derivatives thereof have the structure as shown in the following formula (I'):

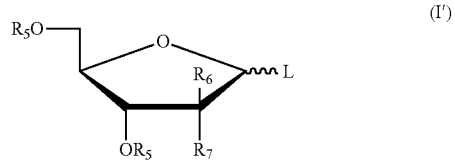

wherein: L, $R_5$, $R_6$, $R_7$ were defined as above.

Preferably, the six-membered rings or the derivatives thereof have the structure as shown in the following formula (II'):

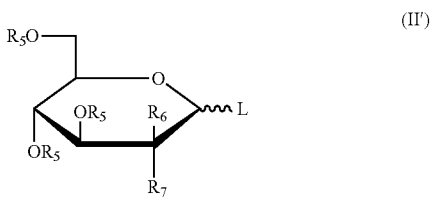

wherein: L, $R_5$, $R_6$, $R_7$ were defined as above.

According to the above method, it may be used to further prepare the β-nucleoside compound, including the following steps:

3) performing a deprotection reaction of the closed β-nucleoside compound as shown in formula (III) or formula (IV) to give the β-nucleoside compound.

In a more specific exemplary embodiment, the present invention provides a method for preparing a closed β-nucleoside compound as shown in formula (V),

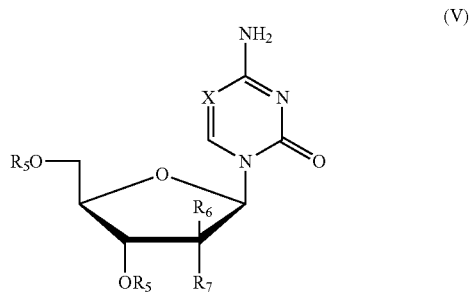

including the following steps:

1) performing a silylation reaction of the compound as shown in formula (VI) in the presence of trimethylsilyl trifluoromethanesulfonate (TMSOTf) to give the compound as shown in formula (VII);

2) performing a direct glycosylation reaction of the reaction liquid of step 1), without being isolated, and the compound of formula (VIII) to give a closed 1-nucleoside compound as shown in formula (V);

the reaction route was as follows:

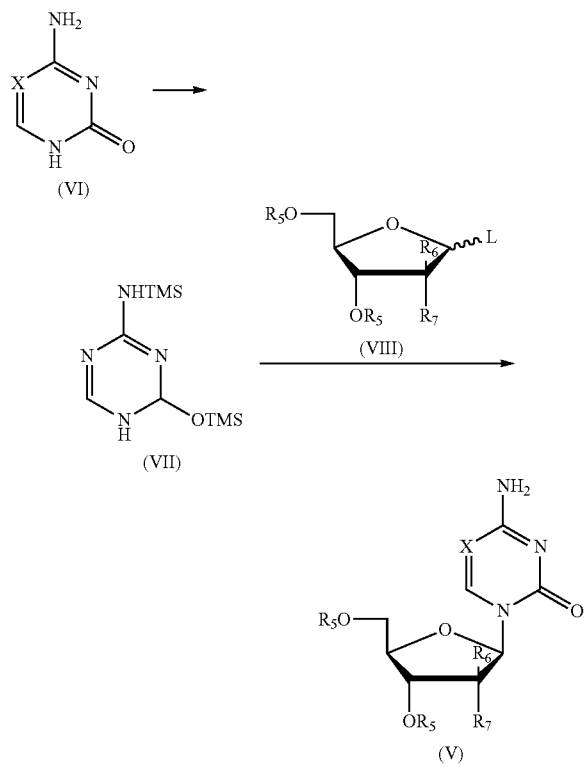

wherein: X is selected from nitrogen, CH, $CR_2$; $R_2$ is selected from hydrogen, $C_{1-6}$ alkyl or a substituted alkyl, halogen; preferably, $R_2$ is selected from hydrogen, methyl, ethyl, propyl, trifluoromethyl, hydroxymethyl, halogen; preferably, X is selected from nitrogen, CH, $C(CH_3)$, $C(CH_2CH_3)$, $C(CH_2CH_2CH_3)$, $C(CH_2OH)$, $C(CF_3)$, $C(F)$, $C(Cl)$, $C(Br)$, $C(I)$;

L is a leaving group; $R_5$ is a hydroxy protecting group; $R_6$ and $R_7$ may independently be selected from hydrogen, halogen, $C_{1-6}$ alkyl or a substituted alkyl, or one of which is $OR_5$.

According to the above method, it may be used to further prepare the f-nucleoside compound as shown in formula (IX), including the following step:

3) performing a deprotection reaction of the closed β-nucleoside compound as shown in formula (V) to give the β-nucleoside compound as shown in formula (IX);

the reaction route was as follows:

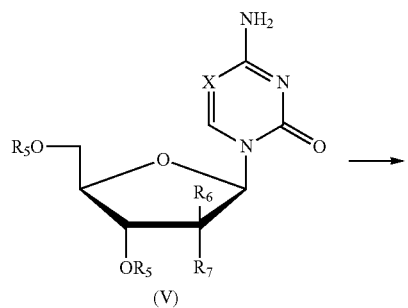

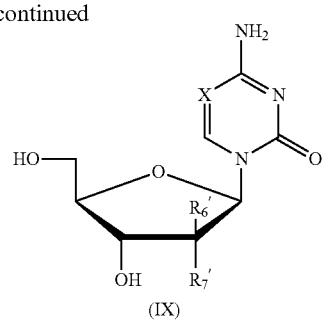

wherein: X, $R_5$, $R_6$, $R_7$ were defined as above; $R_6'$ and $R_7'$ independently indicate hydrogen, halogen, $C_{1-6}$ alkyl or a substituted alkyl, or one of which is OH.

As described above, the method of the present invention generally includes three reaction steps, which are: 1) a silylation reaction, 2) a glycosylation reaction, and 3) a deprotection reaction, respectively.

The silylation reaction of step 1) is carried out in an organic solvent under alkaline condition. The organic solvent may be selected from acetonitrile, dichloromethane, toluene, chloroform, diethyl ether, 1,2-dichloroethane, tetrahydrofuran or the like, preferably is dichloromethane. The base may be selected from triethylamine, 1,8-diazadicycloundec-7-ene (DBU), pyridine, 2,6-dimethylpyridine or the like, preferably is triethylamine.

In step 1), the mole ratio of the nitrogenous base and trimethylsilyl trifluoromethanesulfonate (TMSOTf) may be 1:1~1:5, preferably is 1:1.5~1:3.

In step 1), the mole ratio of nitrogenous base and triethylamine may be 1:2~1:5, preferably is 1:2.5~1:3.5.

The reaction temperature of step 1) may be −20° C.~20° C., preferably is −10° C.~10° C., more preferably is −5~5° C.

The reaction time of step 1) is stopped until the reaction is monitored to be complete, generally is 1~4 hours.

The glycosylation reaction of step 2) is carried out in an organic solvent. The organic solvent may be selected from dichloromethane, toluene, acetonitrile, chloroform, diethyl ether, 1,2-dichloroethane, tetrahydrofuran or the like, preferably is dichloromethane.

In step 2), the mole ratio of the nitrogenous base and furanose or pyranose or derivatives thereof may be 1:1~5:1, preferably is 1.5:1~3:1.

The reaction temperature of step 2) may be −20° C.~25° C., preferably is −10° C.~10° C., more preferably is −5~5° C.

The reaction time of step 2) is stopped until the reaction is monitored to be complete, generally is 1~8 hours.

The deprotection reaction of step 3) may be carried out following the known conventional method, for example hydrolysis in the condition of sodium methoxide/methanol, the reaction temperature of which is generally 20° C.~35° C.

Compared with the traditional production processes, the method of the present invention has significant benefit effects:

1) a large amount of silylation reagents were not necessary for the silylation reaction to reflux by heating, being energy conservation and environment protection;

2) after the silylation reaction, the excess amount of silylation reagents did not have to be removed, and the reaction liquid was directly used in the next step of glycosylation reaction, the key intermediates of the nucleoside compound were produced by a "one-pot" process, the workup operations were very simple, decreasing the duration of the process and improving the production capacity;

3) in the products of the glycosylation reaction, the proportion of β/α configurations was significantly enhanced (about 3.5/1 or higher), significantly enhancing the yield of materials in n-configuration:

4) the final product, the f-nucleoside compound, was high in the total field, with little impurities and high purities.

In summary, the method of the present invention was simple in operation, energy conservation and environmental protection, significantly decreasing the production cost, with good product qualities, being suitable for industrial applications, and the method was generic to be used for preparing various nucleoside compounds.

DETAILED DESCRIPTION

Terms and Definitions

Glycosides: also known as glucosides, the compounds in which sugars or saccharide derivatives, such as aminosugar, uronic acid or the like, bound to another class of non-saccharide materials through the anomeric carbon atom of the sugar. Wherein the non-saccharide moiety is known as aglycone or genin, its linking bond is known as a glycosidic linkage.

N-glycoside: the glycoside linked between the anomeric carbon of saccharide and the nitrogen atom of aglycone is known as N-glycoside. The 1 nucleoside and analogues or nucleoside compounds thereof are mainly N-glycoside compounds.

Nucleoside: the glucoside formed by the condensation between nitrogenous bases and saccharide components is known as nucleoside, which includes purine and pyrimidine glucosides of nucleic acid, further includes other native and synthetic heterocyclic base ribosides, also the compounds with C1 on the sugars linked to the oxygen atom or carbon atom on the heterocyclic base. Compounds linked by the bases and pentose, i.e. compounds formed by the linkage between N-9 of purine or N-1 of pyrimidine and C-1 of ribose or deoxyribose through a 1-glucoside bond, include two classes, ribosenucleoside and deoxyribose nucleoside. Nucleosides constituting RNA are ribosenucleosides, mainly adenosine, guanosine, cytidine and uridine. Nucleosides constituting DNA are deoxyribose nucleosides, mainly deoxyadenosine, deoxyguanosine, deoxycytidine and deoxythymidine.

Nitrogenous base: a class of alkaline organic compounds, which are derivatives of purine and pyrimidine. Purine or analogues thereof includes adenine, urine purine, xanthine, hypoxanthine and other purine derivatives; pyrimidine or analogues thereof includes cytosine, uracil, thymine, 5-methylcytosine, 5-hydroxymethylcytosine, dihydrouracil, and other pyrimidine derivatives. The nitrogenous bases or analogues thereof of the present invention comprise groups that may react with TMSOTf in a silylation reaction, for example amino, hydroxy or the like.

Derivatives: A complex product derived from a simple compound in which the hydrogen atoms or atomic groups were substituted with other atoms or atomic groups.

Five-membered ring saccharides: also known as furanose. Five-membered ring saccharides of the present invention are all the furanoses known in the art. Exemplary five-membered ring saccharides include, but not limited to, D-ribose (e.g., β-D-ribofuranose), 2-deoxy-D-ribose (e.g., 2-deoxy β-D-ribose), D-fructose (e.g., β-D-fructofuranose, α-D-fructofuranose), D-glucose (e.g., α-D-glucofuranose), L-arabinose (e.g., α-L-arabinofuranose), D-arabinose (e.g., α-D-arabinofuranose), apiose (e.g., β-D-apiose), glucuronic acid (e.g., β-D-glucuronic acid) or the like.

Six-membered ring saccharides: also known as pyranose. Six-membered ring saccharides of the present invention are all the pyranoses known in the art. Exemplary six-membered ring saccharides include, but not limited to, D-glucose (e.g., α-D-pyranoglucose, β-D-pyranoglucose), D-galactose (e.g., α-D-galactopyranose), D-mannose (e.g., α-D-mannopyranose), D-xylose (e.g., β-D-xylopyranose), D-fructose (e.g., α-D-fructopyranose), L-sorbose (e.g., α-L-sorbofuranose) and L-galactose (e.g., β-L-galactopyranose).

Exemplary derivatives of five- or six-membered ring saccharide may be products deprived from saccharide molecules in which structures the groups, such as hydrogen atom, carbon atom or hydroxy, were substituted with other atoms or atomic groups. For example, the hydroxy in the molecular structure of saccharide was substituted with a hydrogen atom, halogen, alkyl or the like, the carbon atom in the molecular structure of saccharide was substituted with atoms such as oxygen, sulfur, or the like.

Alkyl: alkyls in the present invention preferably refer to C1-C6 alkyls, for example methyl, ethyl, propyl, butyl, isopropyl, t-butyl, pentyl, hexyl or the like. Substituted alkyl: indicating that the hydrogens on the alkyl were substituted with one or more substituents, for example, the substituents may be hydroxy, halogen, alkyl, amino or the like.

Removable protecting groups: with regard to saccharide molecules, the removable protecting groups in the present invention generally refer to hydroxy protecting groups, also may comprise protecting groups of other groups for saccharide derivatives. Hydroxy protecting groups may be hydroxy protecting groups commonly used in the art, including ester protecting groups (e.g., pivaloyl (t-BuCO, Piv), benzoyl (PhCO), chloracetyl (ClCH$_2$CO) or the like), silyl ether protecting groups (e.g., trimethylsilyl (TMS), triethylsilyl (TES), t-butyl dimethylsilyl (TBS), triisopropylsilyl (TIPS), t-butyl dimethylsilyl (TBDPS) or the like), alkyl ether protecting groups (e.g., methyl ether (Me), benzyl ether (Bn), p-methoxy benzyl ether (PBM), 3,4-dimethoxy benzyl ether (DMB or DMPB), trityl ether, t-butyl ether and allyl ether or the like) and alkoxyalkyl ether protecting groups (e.g., methoxy methyl ether (MOM), methylthio methyl ether (MTM), methoxyethoxy methyl ether (MEM), benzyloxy methyl ether (BOM), trimethylsilyl ethoxy methyl ether (SEM) or the like). The preferable hydroxy protecting groups in the present invention may be: t-butyl dimethyl silyl (TBS), triisopropyl silyl (TIPS), p-chlorbenzoyl (4Cl-Bz), tetrahydrofuryl (THP), benzoyl (Bz) or the like.

Leaving groups: In a nucleophilic substitution reaction, the reactant attacked by the nucleophilic reagent is the substrate, while the atom or atomic group with a pair of electrons broken out from the substrate molecule is known as a leaving group, usually indicated with L. The common leaving groups all may used in the present invention, for example halogen, —OCOR, —OTs, —ONO$_2$, —OH or the like. The preferable leaving groups in the present invention may be: halogen, acetoxy (AcO), methylsulfonyloxy (OMs) or the like.

The method of the present invention is generic to be used for preparing various β-nucleoside compounds, including, but not limited to: Decitabine, Gemciyabine, Azacitidine, Trifluridine, Capecitabine, Fludarabine, Clofarabine, Cladribine, Cytarabine, Vidarabine, Troxacitine, Lamivudine, Zidovudine, Epavudine or the like.

The features and benefits of the present methods will be illustrated in detail below through the preparation embodiments of decitabine, which were provided only for the purpose of exemplary illustration, without being used for confining the applicable scope of the present technical schemes and the protection scope of the present invention.

Preparation route of decitabine in Embodiments 1-3 was shown as below:

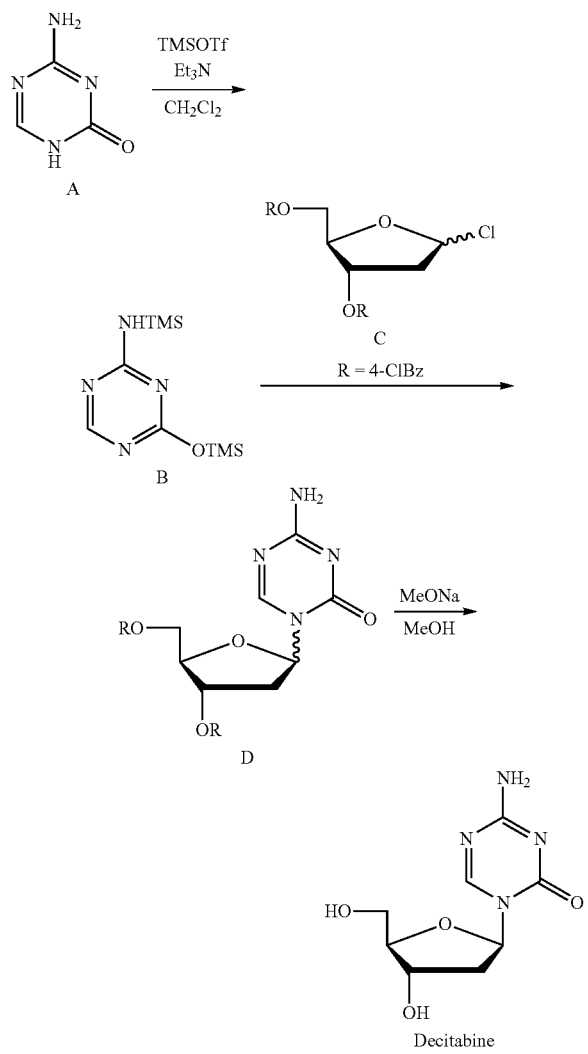

Embodiment 1 Preparation of Decitabine 1-(3,5-di-O-p-chlorobenzoyl-2-deoxy-(3-D-ribofuranose)-5-azacytosine (Intermediate D)

To the reaction flask were added 5-azacytosine 20.0 g and dichloromethane 87.5 mL, into which was added triethylamine 62.1 mL with stirring at 15° C., and dropped trimethylsilyl trifluoromethanesulfonate 118.9 g, continued stirring for 30 min after the system was dissolved to clear. The reaction liquid, without being isolated, was directly added into 1-chloro-3,5-di-O-p-chlorobenzoyl-deoxy-D-ribofuranose 38.3 g, and stirred for about 3 h at 0° C. until the reaction liquid was clear. Triethylamine 37 mL was added to quench the reaction, into which was added dichloromethane and water 500 mL for each respectively, the organic phase was filtered, isolated and concentrated to dry, to the residue of which was added 500 mL water and stirred adequately, suction filtered, and the solid was dried for 6 h at 45° C. in vacuum, crushed, and continued drying for 3 h to give the intermediate D 42.8 g, with a yield of 95.1%. HPLC detection: β-configuration 72.1%, α-configuration 21.0%, total purities 6.9%, the maximum single purity 2.9%.

Decitabine Crude

To the reaction flask were added the above intermediate D 42.8 g, anhydrous methanol 1.3 L, sodium methoxide 2.8 g, stirred for 3 h at 25° C., into which was added 3.0 g glacial acetic acid to quench the reaction, filtered, the filtrate was stirred for 6 h at 0° C. for crystallization to give an off-white solid 8.1 g, with a field of 42.1%. HPLC detection: purity 98.7%, the maximum single purity 0.51%.

Decitabine Refining

To the reaction flask were added the above crude solid 8.1 g, anhydrous methanol 80 mL, which were heated to be clear, filtered while hot, the filtrate was cooled in air to crystallize naturally for 6 h, filtered, the solid was dried for 4 h in vacuum to give the finished decitabine 5.8 g, with a field of 71.6%. HPLC detection: purity 99.8%, the maximum single purity 0.05%.

Embodiment 2 Preparation of Decitabine 1-(3,5-di-O-p-chlorobenzoyl-2-deoxy-β-D-ribofuranose)-5-azacytosine (Intermediate D)

To the reaction flask were added 5-azacytosine 88.5 g and dichloromethane 395 mL, into which was added triethylamine 274.4 mL with stirring at −10° C. Trimethylsilyl trifluoromethanesulfonate 526.3 g was dropped in and continued stirring for 30 min after the system was dissolved to clear. The reaction liquid, without being isolated, was directly added into 1-chloro-3,5-di-O-p-chlorobenzoyl-deoxy-D-ribofuranose 169.6 g, and stirred for about 6 h at −10° C. until the reaction liquid was clear. Triethylamine 164.6 mL was added to quench the reaction, into which was added dichloromethane and water 1500 mL for each respectively, the organic phase was filtered, and concentrated to dry, to the residue of which was added 1500 mL water and stirred adequately, suction filtered, and the solid was dried for 6 h at 45° C. in vacuum, crushed, and continued drying for 3 h to give the intermediate D 185.7 g, with a field of 93.2%. HPLC detection: β-configuration 77.3%, α-configuration 17.6%, the maximum single purity 2.1%.

Decitabine Crude

To the reaction flask were added the above intermediate D 185.7 g, anhydrous methanol 5.6 L, sodium methoxide 11.9 g, stirred for 3 h at 25° C., into which was added 13.2 g glacial acetic acid to quench the reaction, filtered, the filtrate was stirred for 6 h at 10° C. for crystallization to give an off-white solid 32.6 g, with a field of 38.9%. HPLC detection: purity 98.9%, the maximum single purity 0.63%.

Decitabine Refining

To the reaction flask were added the above crude solid 32.6 g, anhydrous methanol 3260 mL, which were heated to be clear, filtered while hot, the filtrate was cooled in air to crystallize naturally for 6 h, filtered, the solid was dried for 4 h in vacuum to give decitabine 22.7 g, with a field of 69.8%. HPLC detection: purity 99.8%, the maximum single purity 0.04%.

Embodiment 3 Preparation of Decitabine

1-(3,5-di-O-p-chlorobenzoyl-2-deoxy-β-D-ribofuranose)-5-azacytosine (Intermediate D)

To the reaction flask were added 5-azacytosine 30.0 g and dichloromethane 87.5 mL, into which was added triethylamine 86.7 mL with stirring at 0° C. Trimethylsilyl trifluoromethanesulfonate 158.4 g was dropped in and continued stirring for 30 min after the system was dissolved to clear. The reaction liquid, without being isolated, was directly added into 1-chloro-3,5-di-O-p-chlorobenzoyl-deoxy-D-ribofuranose 38.3 g, and stirred for about 1.5 h at 5° C. until the reaction liquid was clear. Triethylamine 37 mL was added to quench the reaction, into which was added dichloromethane and water 500 mL for each respectively, the organic phase was filtered, and concentrated to dry, to the residue of which was added 500 mL water and stirred adequately, suction filtered, and the solid was dried for 6 h at 45° C. in vacuum, crushed, and continued drying for 3 h to give the intermediate D 43.5 g, with a field of 96.7%. HPLC detection: β-configuration 80.8%, α-configuration 12.2%, the maximum single purity 1.5%.

Decitabine Crude

To the reaction flask were added the above intermediate D 43.5 g, anhydrous methanol 1.4 L, sodium methoxide 2.9 g, stirred for 3 h at 25° C., into which was added 3.2 g glacial acetic acid to quench the reaction, filtered, the filtrate was stirred for 6 h at 0° C. for crystallization to give an off-white solid 8.9 g, with a field of 45.3%. HPLC detection: purity 99.2%, the maximum single purity 0.25%.

Decitabine Refining

To the reaction flask were added the above crude solid 8.9 g, anhydrous methanol 90 mL, which were heated to be clear, filtered while hot, the filtrate was cooled in air to crystallize naturally for 6 h, filtered, the solid was dried for 4 h in vacuum to give decitabine 6.7 g, with a field of 75.2%. HPLC detection: purity 99.9%, the maximum single purity 0.02%.

Control Embodiment 4 Preparation of Decitabine

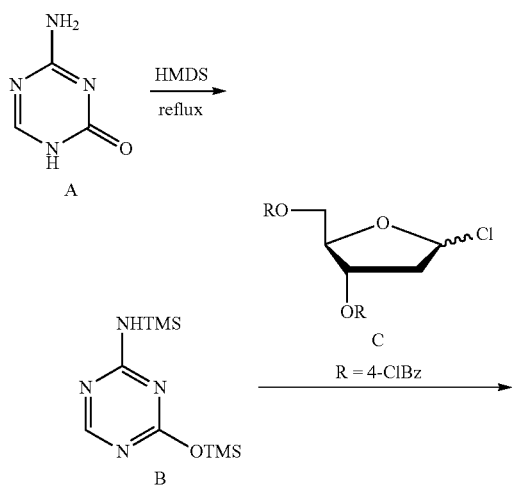

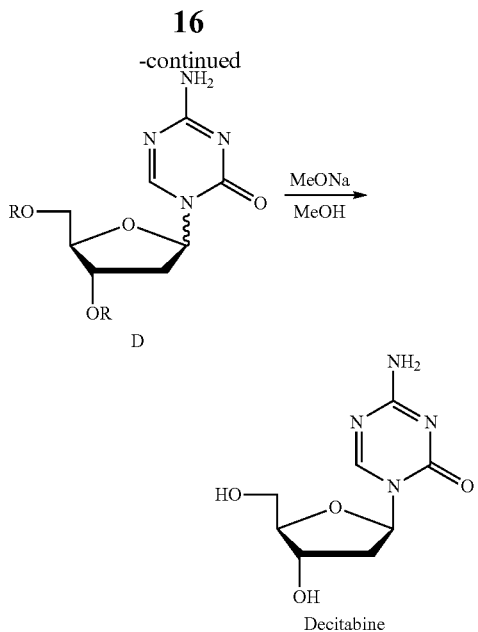

1-(3.5-di-O-p-chlorobenzoyl-2-deoxy-β-D-ribofuranose)-5-azacytosine (Intermediate D)

To the reaction flask were added 5-azacytosine 80 g and hexamethyldisilazane 100 g, into which was added trimethylchlorosilane 50 g with stirring, after the reflux reaction with heating for 6~6.5 h, the excess amount of hexamethyldisilazane was evaporated off under reduced pressure, concentrated to dry and transferred into the reaction flask.

Then, to the reaction flask were added 1-chloro-3,5-di-O-p-chlorobenzoyl-deoxy-D-ribofuranose 102 g, dichloromethane 960 mL, into which was dropped trimethylsilyl trifluoromethanesulfonate 109 g at 20~30° C., and reacted for 13 h at 25±2° C. (the proportion of β/α configuration in the product was about 1:1), into which were added purified water 400 mL and dichloromethane 1080 mL, stirred, filtered, into the organic phase was dropped a 10% sodium bicarbonate solution to neutral, filtered, the organic phase was rinsed and then dried, filtered, the filtrate was concentrated to ¾ the volume of the total amount of the filtrate when the solid resolved was filtered off, continued to concentrate until the filtrate was dry, to the residue of which was added toluene, stirred for 25 min, and then filtered, washed, the filter cake was dried in air for 8 h at room temperature, and then dried in vacuum for 4 h at 40±5° C. to give a solid 24.9 g, with a yield of about 20.7%, HPLC detection: β-configuration 70.5%, α-configuration 20.8%, the total purities 8.7%, the maximum single purity 4.2%.

Decitabine Crude

To the reaction flask were added 1-(3,5-di-O-p-chlorobenzoyl-2-deoxy-β-D-ribofuranose)-5-azacytosine 24.9 g, anhydrous methanol 1479 g and sodium methoxide 1.6 g, reacted for about 4.5 h at 25±2° C., the reaction liquid was adjusted to pH 7.0~7.5 with a 10% solution of acetic acid in anhydrous methanol after the reaction was complete under the monitor of TLC, filtered, and the filtrate was concentrated (the water bath temperature of 40±2° C.) until there was solid being resolved (concentrated to approximately 5% the volume of the filtrate), left for room temperature for crystallization, filtered, washed, and the filter cake was dried at 40±5° C. for 4 h in vacuum to give a solid 4.36 g, with a yield of 38.8%. HPLC detection: purity 98.2%, the maximum single purity 1.2%.

Decitabine Refining

To the reaction flask were added anhydrous methanol 400 mL, Decitabine crude 4.36 g, which were heated to be clear, filtered while hot, the filtrate was cooled to 15~25° C. with stirring to crystallize for 12 h, filtered, the filter cake was washed with anhydrous methanol, dried at 40° C. for 4 h in vacuum to give decitabine 3.18 g, with a yield of 72.9%. HPLC detection: purity 99.7%, the maximum single purity 0.07%.

Embodiment 5 Preparation of Azacitidine Intermediate

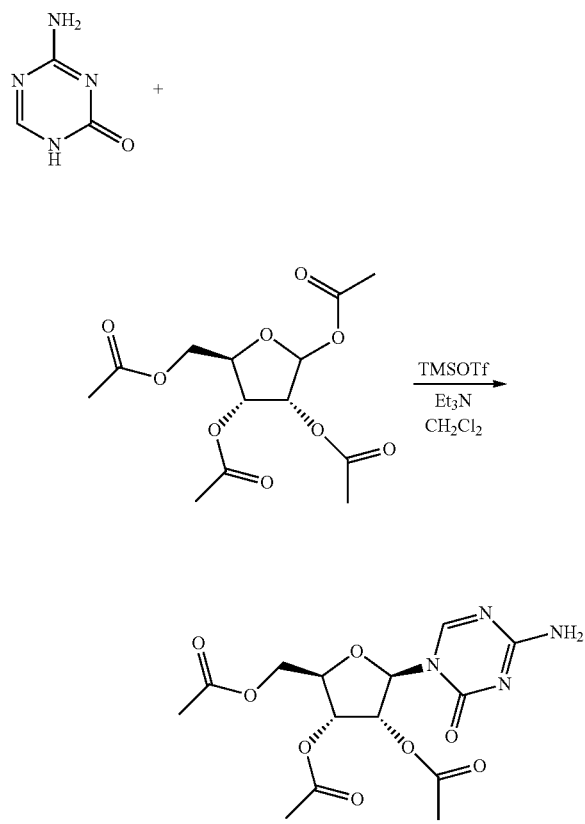

To the reaction flask were added 5-azacytosine 20.0 g and dichloromethane 87.5 mL, into which was added triethylamine 62.1 mL with stirring. Trimethylsilyl trifluoromethanesulfonate 118.9 g was dropped in and continued stirring for 30 min after the system was dissolved to clear. 1,2,3-triacetoxy-5-deoxy-D-ribose 28.4 g was added, stirred for about 1.5 hours until the reaction liquid was clear. Triethylamine 37 mL was added to quench the reaction, into which was added dichloromethane and water 500 mL for each respectively, the organic phase was filtered, and concentrated to dry, to the residue of which was added 500 mL water and stirred adequately, suction filtered, and the solid was dried for 6 hours at 45° C. in vacuum, crushed, and continued drying for 3 hours to give the azacitidine intermediate, 30.7 g, with a yield of 93.0%. HPLC detection: β-configuration 85.3%, α-configuration 8.4%.

Embodiment 6 Preparation of Capecitabine Intermediate

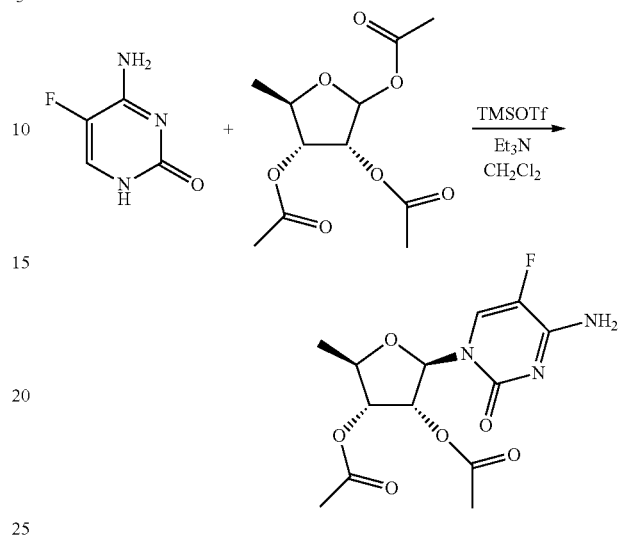

To the reaction flask were added 5-fluorocytosine 23.0 g and dichloromethane 87.5 mL, into which was added triethylamine 62.1 mL with stirring. Trimethylsilyl trifluoromethanesulfonate 118.9 g was dropped in and continued stirring for 30 min after the system was dissolved to clear. 1,2,3,5-tetraacetyl-D-ribofuranose 23.2 g was added, stirred at 5'C for about 1.5 hours until the reaction liquid was clear. Triethylamine 37 mL was added to quench the reaction, into which was added dichloromethane and water 500 mL for each respectively, the organic phase was filtered, and concentrated to dry, to the residue of which was added 500 mL water and stirred adequately, suction filtered, and the solid was dried for 6 hours at 45° C. in vacuum, crushed, and continued drying for 3 hours to give the capecitabine intermediate, 26.7 g, with a yield of 91.0%. HPLC detection: β-configuration 72.3%, α-configuration 20.4%.

Embodiment 7 Preparation of Trifluridine Intermediate

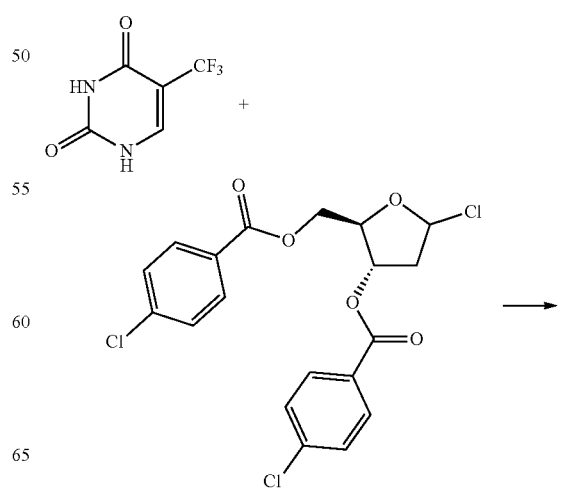

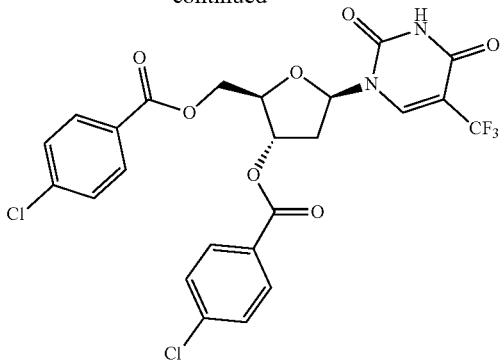

To the reaction flask were added 5-trifluoromethyluracil 32.1 g, dichloromethane 87.5 mL, into which was added triethylamine 62.1 mL with stirring. Trimethylsilyl trifluoromethanesulfonate 118.9 g was dropped in and continued stirring for 30 min after the system was dissolved to clear. 1-chloro-3,5-di-O-p-chlorobenzoyl-deoxy-D-ribofuranose 38.3 g was added, stirred at 0° C. for about 3 hours until the reaction liquid was clear. Triethylamine 37 mL was added to quench the reaction, into which was added dichloromethane and water 500 mL for each respectively, the organic phase was filtered, and concentrated to dry, to the residue of which was added 500 mL water and stirred adequately, suction filtered, and the solid was dried for 6 hours at 45° C. in vacuum, crushed, and continued drying for 3 hours to give the trifluridine intermediate, 46.0 g, with a yield of 90%. HPLC detection: β-configuration 66.3%, α-configuration 27.6%.

The invention claimed is:

1. A method for preparing a β-nucleoside compound, comprising the following steps:
   1) performing a silylation reaction of a nitrogenous base or a nitrogenous base analogue in the presence of trimethylsilyl trifluoromethanesulfonate to give the nitrogenous base or the nitrogenous base analogue protection by trimethylsilyl;
   2) performing a direct glycosylation reaction of the reaction liquid of step 1), without being isolated, and a five- or six-membered ring saccharide or a five- or six-membered ring saccharide derivative protected by a removable protecting group to give a protected β-nucleoside compound; and
   3) performing a deprotection reaction of the protected β-nucleoside compound to give the β-nucleoside compound.

2. The method of claim 1, wherein the nitrogenous base or the nitrogenous base analogue is selected from:

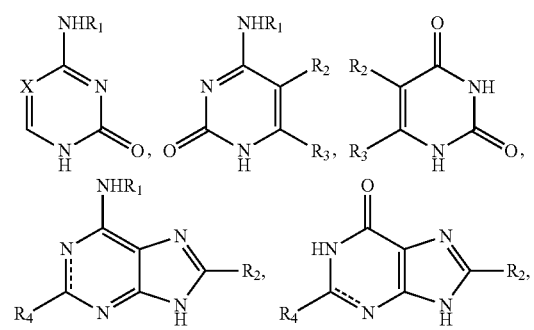

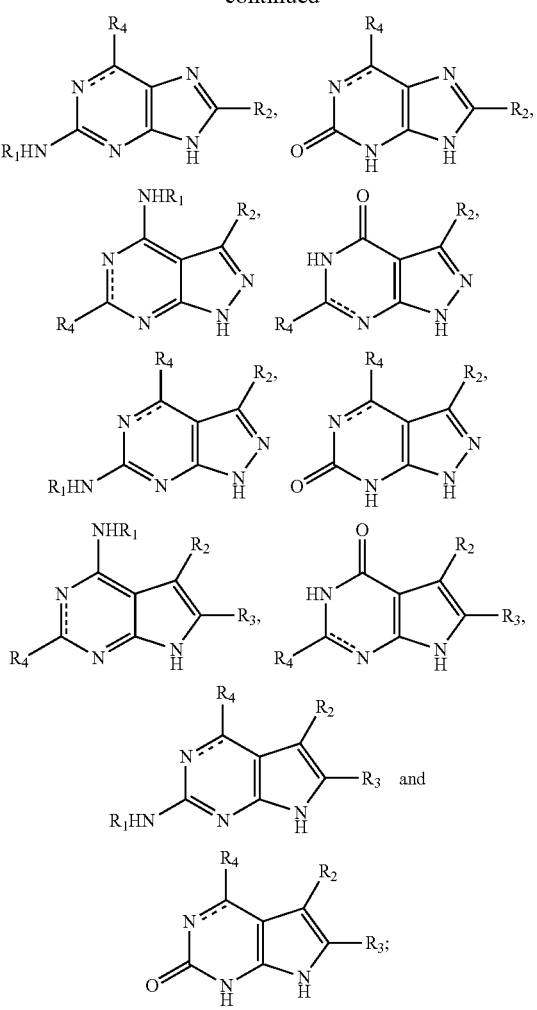

wherein $R_1$ is selected from hydrogen, $C_{1-6}$ alkyl or a substituted alkyl, and $C_{3-8}$ cycloalkyl or a substituted cycloalkyl, X is selected from nitrogen, CH, and $CR_2$, $R_2$ and $R_3$ are independently selected from hydrogen, $C_{1-6}$ alkyl or a substituted alkyl, and halogen, $R_4$ is selected from hydrogen, $C_{1-6}$ alkyl or a substituted alkyl, halogen, amino, $NHR_1$, and carbonyl, and a dotted line bond indicates the presence or absence of a double bond.

3. The method of claim 1, wherein the five-membered ring saccharide or the five-membered ring saccharide derivative being protected by a removable protecting group has the structure as shown in the following formula (I):

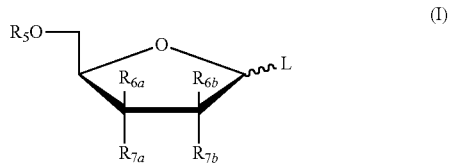

or, the six-membered ring saccharide or the six-membered ring saccharide derivative being protected by a removable protecting group has the structure as shown in the following formula (II):

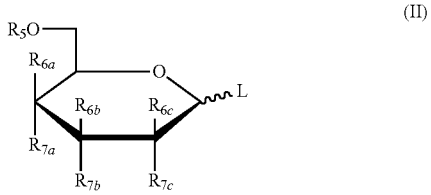

(II)

in formula (I) and formula (II):
L is a leaving group,
$R_5$ is a hydroxy protecting group, and
$R_{6a}$, $R_{6b}$, $R_{6c}$, $R_{7a}$, $R_{7b}$, $R_{7c}$ may independently be selected from hydrogen, halogen, $C_{1-6}$ alkyl or a substituted alkyl, and $OR_5$, $R_{6a}$ is $OR_5$ when different from $R_{7a}$, $R_{6b}$ is $OR_5$ when different from $R_{7b}$, and $R_{6c}$ is $OR_5$ when different from $R_{7c}$.

4. The method of claim 1, wherein the reaction of step 1) is carried out in an organic solvent together with an organic base, the organic solvent is selected from dichloromethane, toluene, acetonitrile, chloroform, diethyl ether, 1,2-dichloroethane, and tetrahydrofuran, and
the organic base is selected from triethylamine, 1,8-diazadicycloundec-7-ene, pyridine, and 2,6-dimethylpyridine.

5. The method of claim 1, wherein in step 1), the mole ratio of nitrogenous base to trimethylsilyl trifluoromethanesulfonate is in a range of 1:1 to 1:5.

6. The method of claim 1, wherein the reaction temperature of step 1) is in a range of −20° C. to 20° C.

7. The method of claim 1, wherein the reaction temperature of step 2) is in a range of −20° C. to 25° C.

8. The method of claim 2, wherein $R_1$ is selected from hydrogen, methyl, ethyl, propyl, and cyclopropyl.

9. The method of claim 2, wherein X is selected from nitrogen, CH, $C(CH_3)$, $C(CH_2CH_3)$, C(F), C(Cl), C(Br), C(I), and $C(CF_3)$.

10. The method of claim 2, wherein $R_2$ and $R_3$ are independently selected from hydrogen, methyl, ethyl, propyl, trifluoromethyl, hydroxymethyl, and halogen.

11. The method of claim 2, wherein $R_4$ is selected from hydrogen, methyl, ethyl, propyl, hydroxymethyl, halogen, amino, and carbonyl.

12. A method for preparing a protected β-nucleoside compound as shown in formula (V),

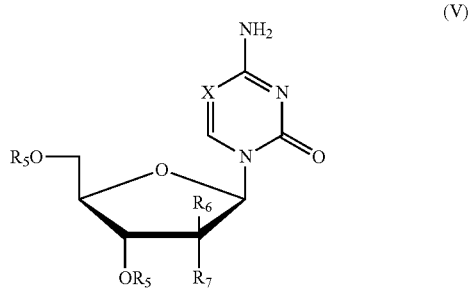

(V)

comprising the following steps:
1) performing a silylation reaction of the compound as shown in formula (VI) in the presence of trimethylsilyl trifluoromethanesulfonate to give the compound as shown in formula (VII);
2) performing a direct glycosylation reaction of the reaction liquid of step 1, without being isolated, and the compound of formula (VIII) to give a protected β-nucleoside compound as shown in formula (V);
the reaction route is as follows:

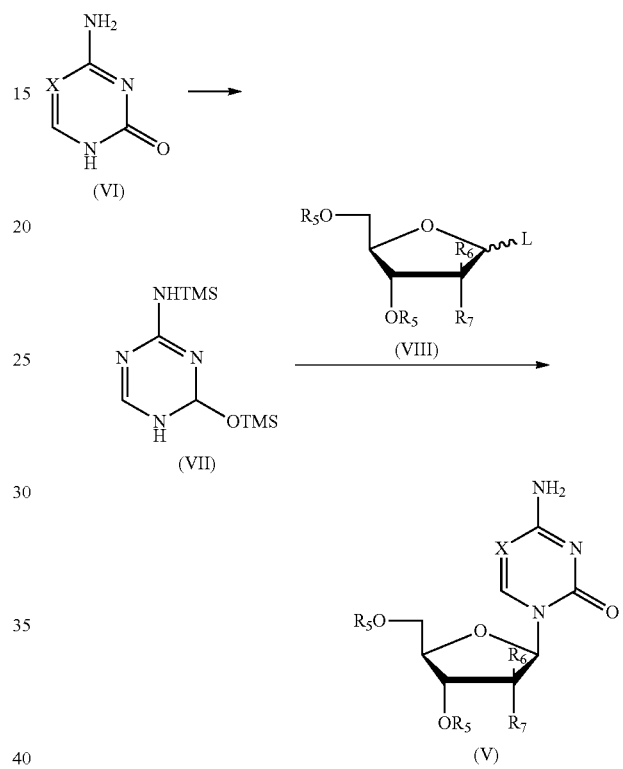

wherein X is selected from nitrogen, CH, and $CR_2$,
$R_2$ is selected from hydrogen, $C_{1-6}$ alkyl or a substituted alkyl, and halogen,
L is a leaving group,
$R_5$ is a hydroxy protecting group, and
$R_6$ and $R_7$ may independently be selected from hydrogen, halogen, and $C_{1-6}$ alkyl or a substituted alkyl, or one of which is $OR_5$.

13. A method for preparing a β-nucleoside compound, comprising performing a deprotection reaction of the protected β-nucleoside compound of claim 4 to give the β-nucleoside compound.

14. The method of claim 13, wherein the β-nucleoside compound is selected from decitabine, gemcitabine, azacitidine, trifluridine, and capecitabine.

15. The method of claim 12, wherein $R_2$ is selected from hydrogen, methyl, ethyl, propyl, trifluoromethyl, hydroxymethyl, and halogen.

16. The method of claim 12, wherein the reaction of step 1) is carried out in an organic solvent together with an organic base, the organic solvent is selected from dichloromethane, toluene, acetonitrile, chloroform, diethyl ether, 1,2-dichloroethane, and tetrahydrofuran, and
the organic base is selected from triethylamine, 1,8-diazadicycloundec-7-ene, pyridine, and 2,6-dimethylpyridine.

17. The method of claim 12, wherein in step 1), the mole ratio of nitrogenous base to trimethylsilyl trifluoromethanesulfonate is in a range of 1:1 to 1:5.

18. The method of claim 12, wherein the reaction temperature of step 1) is in a range of −20° C. to 20° C.

19. The method of claim 12, wherein the reaction temperature of step 2) is in a range of −20° C. to 25° C.

* * * * *